US009029483B2

(12) United States Patent
Azap et al.

(10) Patent No.: US 9,029,483 B2
(45) Date of Patent: May 12, 2015

(54) POLYHEDRAL OLIGOMERIC SILSESQUIOXANE (POSS)-LINKED LIGANDS

(75) Inventors: Cengiz Azap, Frankfurt (DE); Dorit Wolf, Oberursel (DE); Hendrikus Cornelis Louis Abbenhuis, HS Elmond (NL); Gijsbert Gerritsen, SZ Eindhoven (NL); Karol Grela, Warszawa (PL); Jos B. M. Wilting, JD Eindhoven (NL); Kinga Leszczynska, Warszawa (PL); Justyna Czaban, Michalowo (PL); Anna Wojtasiewicz, Warszawa (PL)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/582,010

(22) PCT Filed: Feb. 28, 2011

(86) PCT No.: PCT/EP2011/052885
§ 371 (c)(1),
(2), (4) Date: Nov. 13, 2012

(87) PCT Pub. No.: WO2011/107417
PCT Pub. Date: Sep. 9, 2011

(65) Prior Publication Data
US 2013/0131284 A1 May 23, 2013

(30) Foreign Application Priority Data

Mar. 1, 2010 (EP) ..................................... 10155081
Jun. 15, 2010 (EP) ..................................... 10166004

(51) Int. Cl.
| | | |
|---|---|---|
| C08G 77/398 | (2006.01) |
| C08G 77/388 | (2006.01) |
| C08G 77/395 | (2006.01) |
| C07F 7/21 | (2006.01) |

(52) U.S. Cl.
CPC ................ *C08G 77/398* (2013.01); *C07F 7/21* (2013.01); *C08G 77/388* (2013.01); *C08G 77/395* (2013.01)

(58) Field of Classification Search
CPC ...... C07F 7/21; C08G 77/398; C08G 77/388; B01J 31/0274; B01J 31/1608; B01J 31/2265; B01J 31/2655; B01J 31/2273
USPC .......................................................... 525/474
See application file for complete search history.

(56) References Cited

U.S. PATENT DOCUMENTS

| | | | | | |
|---|---|---|---|---|---|
| 3,373,137 | A | * | 3/1968 | Saam .............................. | 528/33 |
| 6,409,875 | B1 | * | 6/2002 | Giardello et al. ............. | 156/334 |
| 7,910,216 | B2 | * | 3/2011 | Taylor ............................ | 428/447 |
| 2002/0137625 | A1 | * | 9/2002 | Jost et al. ...................... | 502/158 |
| 2004/0068075 | A1 | * | 4/2004 | Lichtenhan et al. ........... | 528/15 |
| 2005/0010012 | A1 | * | 1/2005 | Jost et al. ....................... | 528/34 |
| 2005/0238914 | A1 | * | 10/2005 | Lyu et al. ........................ | 428/690 |
| 2006/0151399 | A1 | * | 7/2006 | Brandts et al. ................. | 210/723 |
| 2007/0122636 | A1 | | 5/2007 | Taylor | |
| 2009/0036297 | A1 | * | 2/2009 | Crudden et al. ............... | 502/158 |
| 2010/0004410 | A1 | * | 1/2010 | Kimura et al. ................. | 526/117 |
| 2010/0317774 | A1 | | 12/2010 | Sugioka | |

FOREIGN PATENT DOCUMENTS

| | | |
|---|---|---|
| EP | 2 535 344 A1 | 12/2012 |
| WO | WO 00/00519 A1 | 1/2000 |
| WO | WO 2008/099904 A1 | 8/2008 |

OTHER PUBLICATIONS

Abbenhuis. "Advances in Homogeneous and Heterogeneous Catalysis with Metal-Containing Silsesquioxanes". Chem. Eur. J. 2000, 6, No. 1, 25-32.*
International Search Report for PCT/EP2011/052885 filed Feb. 28, 2011.
Written Opinion of the International Searching Authority for PCT/EP2011/052885 filed Feb. 28, 2011.
International Preliminary Report on Patentability for PCT/EP2011/052885 filed Feb. 28, 2011.
English language abstract for EP 2 535 344 A1 listed as document B1 above.
Fox, et al., "Use of a Polyhedral Oligomeric Silsesquioxane (POSS)-Imidazolium Cation as an Organic Modifier for Montmorillonite," *Langmuir* 23:7707-7714 (2007).
Kannan, et al., "Polyhedral Oligomeric Silsesquioxane Nanocomposites: the Next Generation Material for Biomedical Applications," *Acc. Chem. Res.* 38:879-884 (2005).
Kantchev, et al., "Palladium Complexes of N-Heterocyclic Carbenes as Catalysts for Cross-Coupling Reactions; a Synthetic Chemist's Perspective," *Angew. Chem. Int. Ed.* 46(16):2768- 2813 (2007).
Lichtenhan, "Polyhedral Oligomeric Silsesquioxanes: Building Blocks for SilsesquioxaneBased Polymers and Hybrid Materials," *Comments Inorg. Chem.* 17(2):115-130 (1995).
Martin, et al., "Palladium-Catalyzed Suzuki Miyaura Cross-Coupling Reactions Employing Dialkylbiaryl Phosphine Ligands," *Acc. Chem. Res.*41(11)1461-1473 (Nov. 2008).
Miyake, et al., "Amphiphilic Hybrid π-Conjugated Polymers Containing Polyhedral Oligomeric Silsesquioxanes," *Macromol. Rapid Commun.* 30(18):1559-1563 (2009).

(Continued)

*Primary Examiner* — Mike M Dollinger
(74) *Attorney, Agent, or Firm* — Law Office of: Michael A. Sanzo, LLC

(57) ABSTRACT

Polyhedral oligomeric silsesquioxanes (POSS) linked ligand of the general formula (I)

$$L[(R^{1a})_{n-1}(SiO_{1.5})_n R^{2a}]_k [(R^{1b})_{n-1}(SiO_{1.5})_n R^{2b}]_l$$
$$[(R^{1c})_{n-1}(SiO_{1.5})_n R^{2c}]_m \quad (I)$$

in which $(R^{1a,b,c})_{n-1}(SiO_{1.5})_n$ is a polyhedral oligomeric silsesquioxanes (POSS) with n=4, 6, 8, 10, 12, 14, 16 or 18 and $R^{1a}$, $R^{1b}$, $R^{1c}$ is each independently selected from the group consisting of same or different branched or linear $C_1$-$C_{20}$ alkyl chains, cyclo alkyl, $C_1$-$C_{20}$ alkoxy, aryl, aryloxy, heteroaryl and arylalkyl groups, k, l, m is 0 or 1 provided that k+l+m≥1, $R^{2a}$, $R^{2b}$, $R^{2c}$ is a spacer that binds the polyhedral oligomeric silsesquioxane (POSS) to the ligand L and ligand L is an uncharged electron donor.

16 Claims, No Drawings

(56) References Cited

OTHER PUBLICATIONS

Newmann, et al., "An Efficient and Practical Sequential One-Pot Synthesis of Suprofen, Ketoprofen and Other 2-Arylpropionic Acids," *Adv. Synth. Catal.* 350:2437-2442 (2008).

Newmann, et al., "A General Synthesis of Diarylketones by Means of a Three-Component Cross-Coupling of Aryl and Heteroaryl Bromides, Carbon Monoxide, and Boronic acids," *Chem. Eur. J.* 14:3645-3652 (2008).

Ropartz, et al., "Phosphine-containing carbosilane dendrimers based on polyhedral silsesquioxane cores as ligands for hydroformylation reaction of oct-1-ene," *Journal Molecular Catalysis A: Chemical* 182-183:99-105 (2002).

English language translation of Chinese Office Action for corresponding Chinese patent application No. 201180011723.6 (May 21, 2014).

Erhui, et al., "Progress in nanohybrid materials based on polyhedral oligomeric silsesquioxanes". *New Chemical Materials* vol. 36 No. 8, p. 28, section 2.1.2 (Aug. 2008).

Franchini, et al., "Influence of POSS structure on the fire retardant properties of epoxy hybrid networks," *Polymer Degradation and Stability* 94(10):1728-1736 (Oct. 2009).

Garcia, et al., "Modification of Chiral Dimethyl Tartrate Through Transesterification: Immobilization on POSS and Enantioselectivity Reversal in Sharpless Asymmetric Epoxidation," *Chirality* 22(7):675-683 (published online Dec. 2009).

Hendan, et al., "Silsesquioxanes as Models of Silica Supported Catalyst I. [3-(Diphenylphosphino)propyl]-hepta[propyl][octasilsesquioxane] and [3-Mercapto-propyl]hepta[propyl][octasilsesquioxane] as Ligands for Transition-Metal Ions," *Applied Organometallic Chemistry* 13(4):287-294 (Apr. 1999).

Shockey, et al., "Functionalized Polyhedral Oligosilsesquioxane (POSS) Macromers: New Graftable Poss Hydride, Poss α-Olefin, POSS Epoxy, and POSS Chlorosilane Macromers and POSS-Siloxane Triblocks," *Applied Organometallic Chemistry* 13(14):311-327 (Apr. 1999).

Strachota, et al., "Formation of nanostructured epoxy networks containing polyhedral oligomeric silsesquioxane (POSS) blocks," *Polymer* 48(11):3041-3058 (May 2007).

Yu, et al., "Sequential Thiol-Ene/Thiol-Ene and Thiol-Ene/Thiol-Yne Reactions as a Route to Well-Defined Mono and Bis End-Functionalized Poly(N-isopropylacrylamide)," *Journal of Polymer Science: Part A: Polymer Chemistry* 47(14):3544-3557 (Jun. 2009).

Zhang, et al., "Homogenous polyhedral oligomeric silsesquioxane (POSS)-supported Pd-diimine complex and synthesis of polyethylenes end-tethered with a POSS nanoparticle via ethylene "living" polymerization," *Chemical Communications* 10:1178-1180 (Sep. 2009).

\* cited by examiner

POLYHEDRAL OLIGOMERIC SILSESQUIOXANE (POSS)-LINKED LIGANDS

The work leading to this invention has been received funding from the European Community 7th Framework programme under grant agreement no. NMP3-SL-2008-214095.

CROSS REFERENCE TO RELATED APPLICATIONS

The present application is US national stage of international application, PCT/EP2011/052885 which had an international filing date of Feb. 28, 2011, and which was published in English under PCT Article 21(2) on Sep. 9, 2011. Priority is claimed to European application EP 10155081.2, filed on Mar. 1, 2010 and to European application EP 10166004.1, filed on Jun. 15, 2010. These prior applications are incorporated by reference herein in their entirety.

FIELD OF THE INVENTION

The invention relates to polyhedral oligomeric silsesquioxane (POSS)-linked ligands and their salts, synthesis of said polyhedral oligomeric silsesquioxane (POSS)-linked ligands and their application in transition metal catalyzed cross-coupling reactions exemplified by Palladium-based catalyst systems.

BACKGROUND OF THE INVENTION

Homogeneous transition metal catalyzed reactions have been refined into important processes for the synthesis of high-valued organic compounds (a) G. W. Parshall, S. D. Ittel, *Homogeneous Catalysis: The Application and Chemistry by Soluble Transition Metal Complexes*, Wiley VCH, 1992; b) F. Diederich, P. J. Stang *Metal Catalyzed Cross-Coupling Reactions*; Wiley-VCH: Weinheim 1998. c) M. Beller, C. Bolm, *Transition Metals for Organic Synthesis*; Wiley-VCH: Weinheim 1998). From these, Palladium-catalyzed cross-coupling reactions have emerged as one of the most important reactions both in industry and academia. In recent years there have been numerous contributions in this area (a) J. Tsuji, *Palladium Reagents and Catalysts: Innovations in Organic Synthesis*; Wiley: Chicester, 1995.).

Palladium catalysts bearing an N-heterocyclic carbene and sterically demanding phosphine ligands display the most robust and active catalytic systems to date (review on Pd-complexes of N-heterocyclic carbenes for cross-coupling reactions: M. G. Organ et al. *Angew. Chem. Int. Ed.* 2007, Vol 46, 16, 2768-2813, recent examples of applications of phosphine ligands: M. Beller, *Adv. Synth. Catal.* 2008, 350, 2437-2442, M. Beller, *Chem.—Eur. J.* 2008, 14, 3645-3652; S. L. Buchwald *Acc. Chem. Res.* 2008, Vol. 41, 11, 1461-1473 and references cited therein).

However, the application of homogeneous transition metal catalysts can result in soluble metal contamination. These soluble metals can be detrimental to product quality and product yield. In the case of active pharmaceutical ingredient (API) development, the metal catalyst must be removed to a regulated level. This can be achieved by e.g. chemical metal scavenging substances or techniques where the metal residues are removed by physical methods such as extraction, distillation or precipitation.

From the industrial point of view one attractive physical method constitutes membrane filtration technology in which the organic materials are removed by filtration and the metal catalyst remains within the membrane sphere.

Methods for removing the catalyst by either chemical or physical methods are usually very complex and thus expensive or in the case of membrane filtration can't be employed because there are no membranes available with the required selectivity.

It is thus an object of the present invention to provide ligands and/or their salts as well as metal complexes comprising said ligands for homogeneous catalysed reactions with which the disadvantages of the prior art are at least reduced and that allow simple and cost efficient separation of metal complexes and reaction solution.

This object is achieved with polyhedral oligomeric silsesquioxanes (POSS)-linked ligands according to general formula I and the corresponding salts according to general formula II as well as bidentate polyhedral oligomeric silsesquioxanes (POSS) linked ligands according to general formula III and the corresponding salts according to general formula IV.

The POSS linked ligands according to the invention thus do not necessarily have to be monodentate. They could also be used as bidentate or tridentate ligands which are connected by linker molecules e.g. alkyl chains. The POSS linked ligands in a bidentate or tridentate molecule can be identical or different from each other.

Since for the production of metal complexes often the salts of the ligands are used the invention also encompasses the salts of the POSS linked ligands. Said salts are obtained by the simple reaction of a leaving group containing POSS-connected alkyl residue with the corresponding ligand. The leaving group may e.g. be halogen, sulfonate, triflate, acetate or phosphate.

(I)

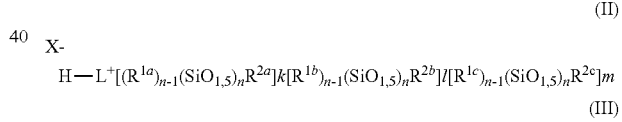
(II)

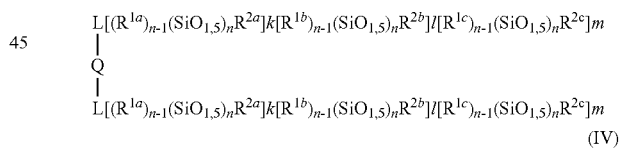
(III)

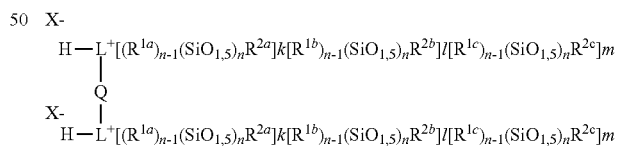
(IV)

in which $(R^{1a,b,c})_{n-1}(SiO_{1.5})_n$ is a polyhedral oligomeric silsesquioxane (POSS) with n=4, 6, 8, 10, 12, 14, 16 or 18 and $R^{1a}, R^{1b}, R^{1c}$ is each independently selected from the group consisting of same or different branched or linear $C_1$-$C_{20}$ alkyl chains, cyclo alkyl, $C_1$-$C_{20}$ alkoxy, aryl, aryloxy, heteroaryl and arylalkyl groups, k, l, m is 0 or 1 provided that k+l+m≥1, $R^{2a}, R^{2b}, R^{2c}$ is a spacer that binds the polyhedral oligomeric silsesquioxane (POSS) to the ligand L, $R^{2a}, R^{2b}, R^{2c}$ is each independently selected from the group consisting of linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, $C_1$-$C_{20}$ alkyl halogenide, annulated aryl or heteroaryl, $C_3$-$C_{10}$ cyclic alkyl groups which in turn may each be further substituted with one or more groups selected from hetero atom or aryl groups, ether, polyether polythioether, amino, aryl bridged alkyl chain where the aryl moiety can include further substitution pattern and in structures I and III ligand L is an uncharged electron donor, whereas in structures II and IV $L^+$ is a protonated species of L, H is hydrogen, Q is a branched or linear substituted or unsubstituted alkyl chain with a chain length ranging from $C_1$ to $C_{20}$. Furthermore Q may be a unsubstituted or substituted cyclic alkyl, aryl or heteroaryl group where the aryl and heteroaryl moieties can include further substitution pattern.

$X^-$ is a mono- or polyvalent organic or inorganic anion

The phrase "polyhedral oligomeric silsesquioxanes (POSS)" as used herein means that the POSS molecule can be regarded in a simplified manner as a roughly 3-dimensional geometric structure with flat faces and straight edges in which the Si-atoms are located at the corners of the structure.

For example for n=6 the POSS molecule is a pentahedral structure in the shape of a triangular prism with 6 Si atoms located at the corners of the structure.

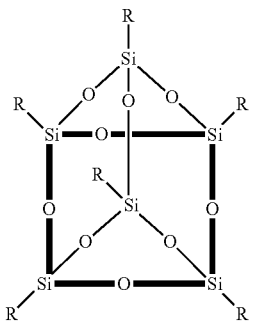

In another example with n=8 the POSS molecule is a hexahedral structure in the shape of a cube with 8 Si atoms located at the corners of the structure. It should be noted that substituents R in the structure shown above and in the following structures are not all identical. One substituent R is needed as spacer that binds the POSS molecule to the ligand L, i.e. one of the substituents R equals substituent $R^2$.

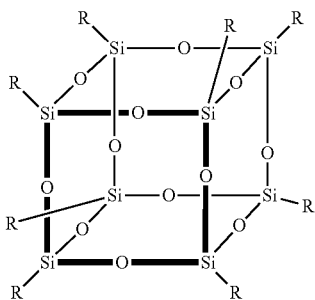

For n=10 the POSS molecule is a heptahedral structure in the shape of a pentagonal prism with 10 Si atoms located at the corners of the structure.

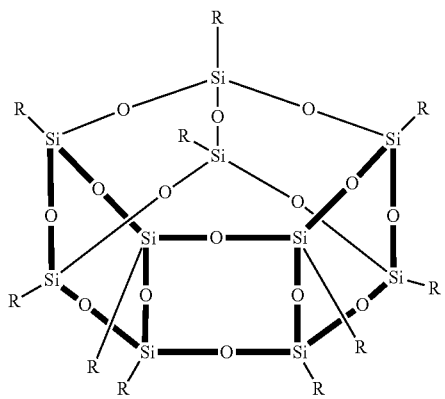

POSS molecules are known to the skilled artisan since the first synthesis by Lichtenhan et al. in 1995 (J. D. Lichtenhan Comments. Inorg. Chem. 1995, Vol. 17, No. 2, pp. 115-130; A. M. Seifalian, Acc. Chem. Res. 2005, Vol 38, No. 11 879-884). The POSS molecules which are also referred to as POSS-cages display rigid and robust structures due to the strong framework resulting from their shorter bond.

The spacer $R^{2a}$, $R^{2b}$, $R^{2c}$ bonds to the polyhedral oligomeric silsesquioxanes (POSS) molecule over a Si or O atom of the POSS molecule. The spacer $R^{2a}$, $R^{2b}$, $R^{2c}$ can bond to the ligand L via all bonds that are known to the skilled artisan preferably via C, O, N or S:

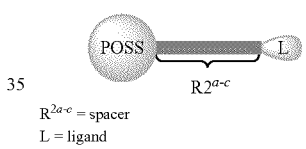

$R^{2a-c}$ = spacer
L = ligand

Surprisingly it was found that polyhedral oligomeric silsesquioxanes (POSS) molecules with the generic formula $((R^1)_{n-1}(SiO_{1.5})_n R^2)$ can be bonded to ligands and thus be used for enlarging the catalyst structure in order to enable membrane filtration separation. $R^1$, $R^2$ is a generic term that also includes the a, b, c species as previously defined. One drawback of mass dependent membrane-filtration methodology is that a certain mass difference between the used catalyst and the substrates (and products) is required, so that retention of the catalyst is possible while product is transported through the membrane. Thus, most filtration techniques are limited to small sized molecules with a much lower molecular mass than the catalyst, since commercially used catalysts are of molecular weight between 400 and 900 g/mol.

As a solution to this problem, POSS-enlarged ligands for homogeneous catalyst systems are presented in this invention. These catalysts preferably have molecular weights ranging from 1500 to 3000 g/mol. Due to the increased mass of the catalyst a mass difference between catalyst and product can be reached that is sufficient to separate catalyst and product by membrane filtration. Products of a much larger weight range can thus be separated from a homogeneous catalyst comprising POSS enlarged ligands. The increased mass allows retention of the catalyst, passage of the product and final isolation of larger molecules by filtration. With respect to the production processes of intermediates and final products for the pharmaceutical industry, these new catalyst systems are of high-interest.

In the context of the present invention ligands are chemical compounds comprising one or several atoms. A coordinate bond is formed when one or several atoms of a ligand contribute their electrons or their orbitals filled with electrons to another atom. The ligand contributing the electrons is designated as the "donor" whereas the atom accepting the free electrons or the electrons from a filled orbital of the donor is designated as the "acceptor". Ligand-atoms contributing the electrons or orbitals for the coordinate bonds, usually, are main-group-elements from groups III-VII with low oxidation numbers (e.g. C, N) Acceptors on the other hand, typically, are metal atoms with high oxidation numbers, e.g. z. B. Pd(II), Ru(III). An uncharged donor, thus, is a ligand without net-charge that contributes electrons or orbitals filled with electrons for a coordinate bond with an acceptor. Examples of uncharged donors are (wherein the two dots preceeding the letter depict the electrons participating in the coordinate bond):

PH3P:, $R_2N$:, $Ph_3As$:, or:

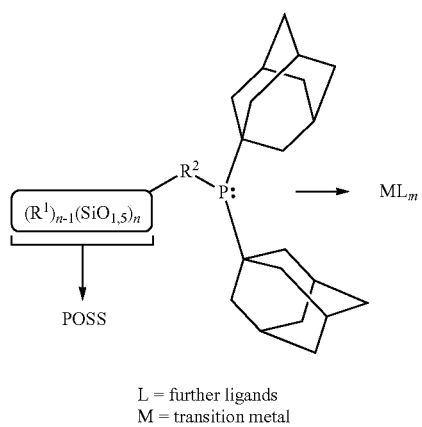

L = further ligands
M = transition metal

Importantly, carbon too can act as an uncharged (electron) donor. Mostly found as carbene, the carbon atom bears a pair of electrons in an orbital. These electrons are provided for an uncharged sigma bond with the metal center. This is usually expressed by structures drawn as:

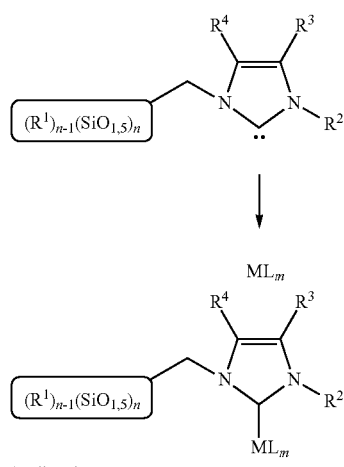

L = further ligands
M = transition metal

Charged (electron) donors on the other hand carry a net-charge, i.e. cationic donors bear a positive net-charge and anionic donors bear a negative net-charge.

The polyhedral oligomeric silsesquioxane (POSS)-linked ligands and their salts according to the invention can be considered as "nanoparticles or nanocomposites" due to the fact that their size ranges several nanometers.

Even more surprisingly the POSS linked ligands and their salts according to the present invention are on the one hand soluble which is a precondition for their use in homogeneous catalysis and on the other hand filtratable by membrane filtration methods which is a precondition for their cost efficient and simple removal out of a reaction solution. The use of POSS linked ligands or their salts for homogeneous transition metal catalysts therefore combine in an unexpected manner the advantages of homogeneous catalysis, i.e. high accessibility and high activity with the advantage of a simple removal of the catalyst. The POSS linked ligands or their salts therefore allow for the first time the use of homogeneous transition metal catalysts for continuous processes.

The POSS linked ligands in particular their salts have another advantage over ligands or their salts that are not linked to a POSS molecule. Ligand salts having very low solubility in common organic solvents e.g. toluene show significantly improved solubility when they are linked to a POSS molecule. Compared to imidazolium or phosphonium salts which are used for the construction of transition metal catalysts in homogeneous processes, POSS enlarged salts thereof show drastically enhanced solubilities. The enhanced solubility will greatly facilitate the construction of the transition metal catalysts with these ligand salts in terms of ease of reaction performance. Tests showed that in toluene, which is widely used as solvent in commercial applications, POSS-free imidazolium and phosphonium salts are unsoluble whereas the POSS-derivatives can be dissolved very well.

In preferred embodiments the present invention also pertains the application of novel nanoparticle linked phosphine and N-heterocyclic carbene ligands in cross-coupling reactions, where nanometer sized polysilsesquioxane cubes or other polyhedral shapes as mentioned above serve as nano-anchors.

Preferred substituents $R^{1a}$, $R^{1b}$, $R^{1c}$ of the polyhedral oligomeric silsesquioxanes (POSS) linked ligands according to the invention are unsubstituted branched alkyl chains. These substituents ensure solubility of the POSS architecture in various organic polar and non-polar solvents. It is thus important that the preferred substituents $R^{1a-c}$ bear no functional groups such as e.g. OH, NH or COOH. Otherwise chemical interaction between these functional groups and the catalyst or other reagents that are employed within the application could result especially when L is a N-heterocyclic carbene. Finally the said POSS-substituents contribute to further enlargement of the POSS-moiety.

In another preferred embodiment of the invention the spacer molecules $R^{2a}$, $R^{2b}$, $R^{2c}$ are linear $C_1$-$C_{20}$ alkyl, more preferably linear $C_3$-$C_{10}$ alkyl.

In yet another preferred the polyhedral oligomeric silsesquioxanes (POSS) ligands are of the general formula (II)

$$L[(R^{1a})_{n-1}(SiO_{1.5})_n R^{2a}]_k \tag{II}$$

in which $R^{1a}$, n, $R^{2a}$ have the same meaning as described above and k=1.

The ligand L is preferably selected from the group consisting of N-heterocyclic carbene, amine, imine, phosphine, stibine, arsine, carbonyl compound, carboxyl compound, nitrile, alcohol, ether, thiol or thioether.

More preferably ligand L of the polyhedral oligomeric silsesquioxanes (POSS) ligand according to the invention is a N-heterocyclic carbene. N-heterocyclic carbenes are extremely reactive intermediates that are very difficult to isolate. Further, many substances destroy the N-heterocyclic carbenes through chemical interaction. It is thus surprising that it is possible to link the oligomeric silsesquioxanes (POSS) molecules with a N-heterocyclic carbene ligand.

Most preferably the polyhedral oligomeric silsesquioxanes (POSS) linked N-heterocyclic carbenes or their salts are of the following structures:

salts

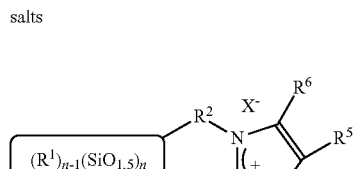

III

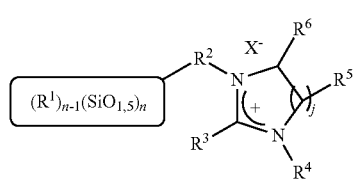

IV carbenes

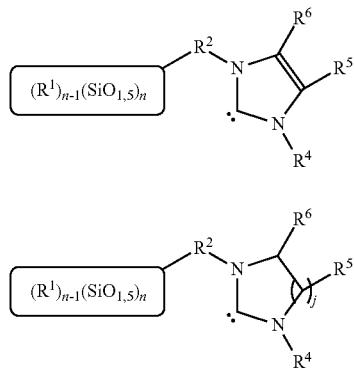

IIIa

IVa

Additionally preferred are polyhedral oligomeric silsesquioxanes (POSS) linked triazole-carbenes or their salts that are of the following structures:

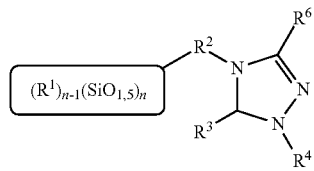

V

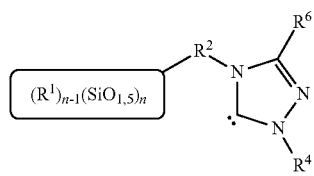

Va

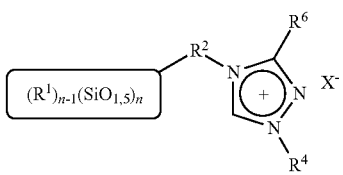

V'

VI

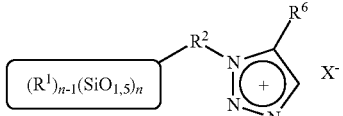

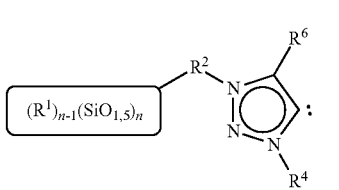

VIa wherein:

$R^1$ is the same or different branched or linear $C_1$-$C_{20}$ alkyl chains, cyclo alkyl, $C_1$-$C_{20}$ alkoxy, aryl, aryloxy, arylalkyl groups, substitution pattern also includes further POSS fragments having the same or different structure. $R^1$ may also be multiply substituted halogen alkyl, unsubstituted or substituted aryl groups and substituted alkyl groups, aryloxy, hetaryloxy groups.

$X^-$ is a mono or polyvalent organic or inorganic anion.

The spacer molecule $R^2$ that binds the POSS-molecule and to the N-atom of the N-heterocyclic carbene is selected from the group consisting of $C_1$-$C_{20}$ linear or branched alkyl chain, ether, polyether polythioether, amino, aryl bridged alkyl chain where the aryl moiety can include further substitution pattern, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, $C_1$-$C_{20}$ alkyl halogenide, annulated aryl or heteroaryl, $C_3$-$C_{10}$ cyclic alkyl groups which in turn may each be further substituted with one or more groups selected from hetero atom or aryl groups. Additionally the alkyl chain can contain further complexing moieties like phosphine derivatives.

j is preferably 1-5 giving ring sizes of the heterocyclic ligand ranging from 5 to 8. In case of j=1 the most preferred heterocyclic ring moiety is imidazole. In case that j is 2, 3, 4 or 5 the additional substituents have the same meaning as $R^3$, $R^4$, $R^5$ and $R^6$.

$R^3$, $R^4$, $R^5$ and $R^6$ are the same or independent from each other and selected from the group consisting of hydrogen, linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, multiply substituted halogen aryl or heteroaryl, $C_1$-$C_{20}$ alkyl halogenide, multiply substituted halogen alkyl, annulated aryl or heteroaryl, $C_3$-$C_{10}$ cyclic alkyl groups which in turn may each be further substituted with one or more groups selected from hetero atom or aryl groups.

In addition, $R^5$ or $R^6$ may also depict a POSS-molecule with the structure $(R^1)_{n-1}(SiO_{1.5})_n$ linked by a spacer molecule $R^2$ to a carbon atom of the N-heterocyclic carbenes or their salts of the above given structures.

Preferably the N-heterocyclic carbene contains an additional $C_1$-$C_{20}$ alkyl chain-bridged POSS-moiety leading to a N-heterocyclic carbene ligand with two POSS molecules of the structure as depicted in formula VII and VIIa:

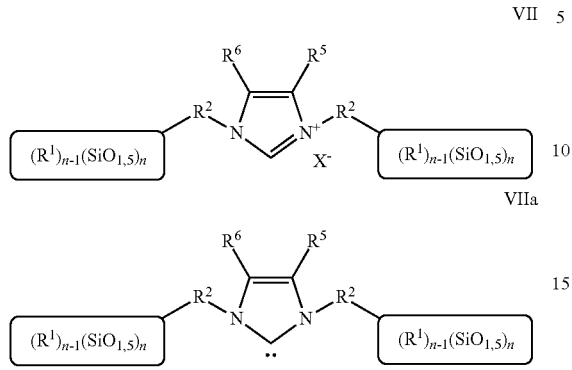

R² is preferably an alkyl chain. Both R² alkyl chain lengths can be independently or the same where both R² enclose branched and linear $C_1$-$C_{20}$ (n=1-20) alkyl chains.

Additionally the POSS linked N-heterocyclic carbene may be connected via an alkyl chain R⁷ to another POSS linked N-heterocyclic carbene, e.g. POSS linked imidazole thus leading to a dimeric structure as depicted in formula VIII and VIIIa:

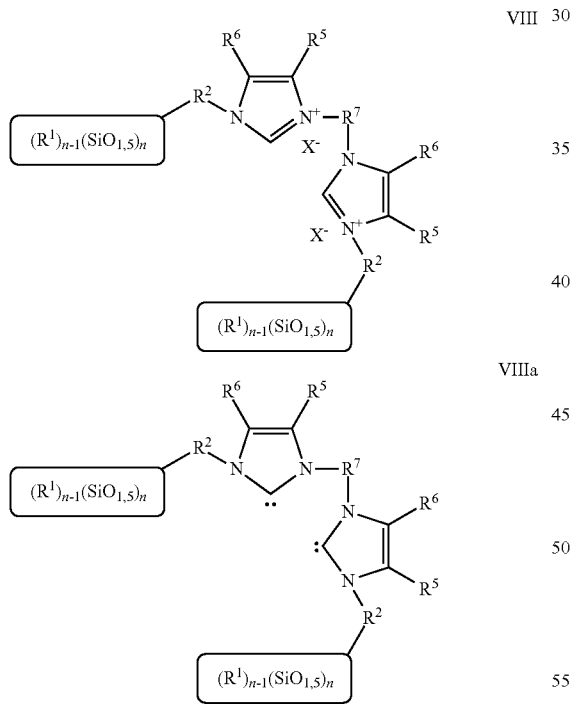

Wherein R⁷ is substituted or unsubstituted linear or branched $C_1$-$C_{10}$ alkyl chain.

Moreover, any of the ligands substituents R³-R⁶ may further include one or more functional groups. Examples of suitable functional groups include but are not limited to: hydroxyl, amine, amide, nitrile, thiol, thioether, ketone, aldehyde, ester, ether, imine, nitro, carboxylic acid, disulfide, carbonate and halogen.

Further preferred embodiments include the following structures:

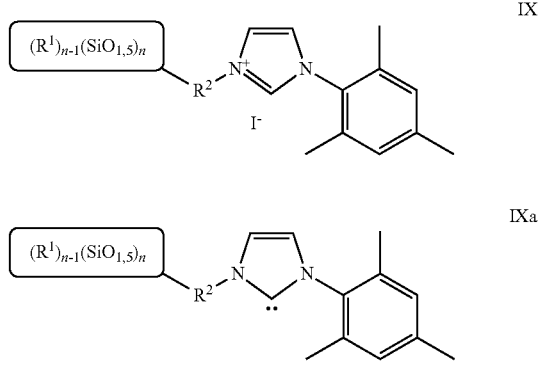

Unsymmetrical substituted N-heterocyclic carbenes and the corresponding salts thereof contain one $C_1$-$C_{20}$ alkyl chain-bridged POSS-moiety on one N-atom and a 2,4,6-trimethylbenzene (mesityl) substituent on the other N-atom of the imidazole moiety (formulas IX and IXa).

Preferred embodiments of POSS linked triazole ligands are of following structures:

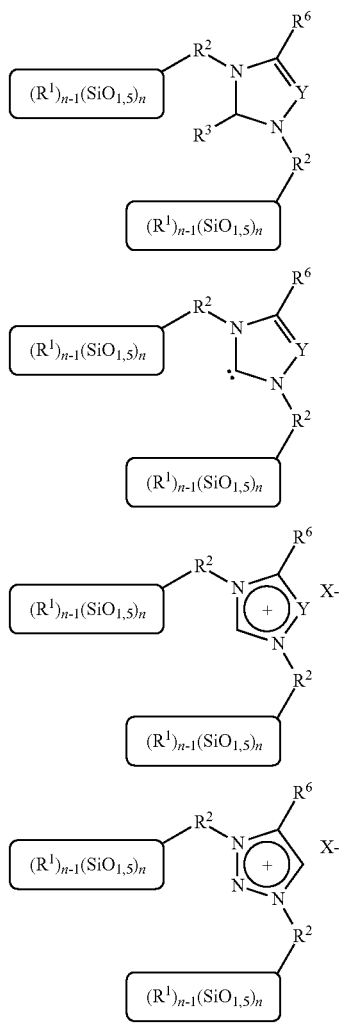

-continued

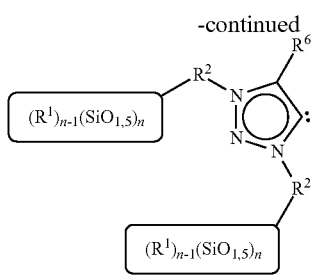

In another preferred embodiment of the polyhedral oligomeric silsesquioxanes (POSS) linked ligands according to the invention ligand L is a phosphine or a salt thereof.

The phosphine-based ligands or their salts disclosed in this present patent are preferably of general formula:

X

Xa wherein:

$R^1$ is the same or different branched or linear $C_1$-$C_{20}$ alkyl chains, cyclo alkyl, $C_1$-$C_{20}$ alkoxy, aryl, aryloxy, arylalkyl groups, substitution pattern also includes further POSS fragments having the same or different structure. $R^1$ may also be multiply substituted halogen alkyl, unsubstituted or substituted aryl groups and substituted alkyl groups, aryloxy, hetaryloxy groups.

$X^-$ is a mono- or polyvalent organic or halide anionic ion.

$R^8$ and $R^9$ are the same or different branched or linear $C_1$-$C_{20}$ alkyl chains, cyclo alkyl, $C_1$-$C_{20}$ alkoxy, aryl, aryloxy, arylalkyl groups.

Most preferably $R^8$ and $R^9$ are adamantyl radicals XI or XIa where the phosphorus atom in XI is bound at the 2-position and in XIa at the 1-position.

XI

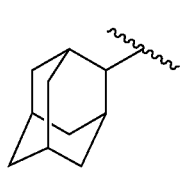

XIa

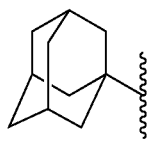

The spacer $R^2$ between the POSS-molecule and the attached phosphorus is selected from the group consisting of $C_1$-$C_{20}$ linear or branched alkyl chain, ether, polyether polythioether, amino, aryl bridged alkyl chain where the aryl moiety can include further substitution pattern.

In another preferred embodiment $R^2$, $R^8$ and $R^9$ contain aryl groups, where the aryl groups are bonded to the P-atom and the POSS moieties is attached via alkyl chains $R^{10}$ that are connected to the said aryl groups as depicted in formula XII. Alkyl chain $R^{10}$ connected to the aryl group thus corresponds to spacer $R^2$.

XII

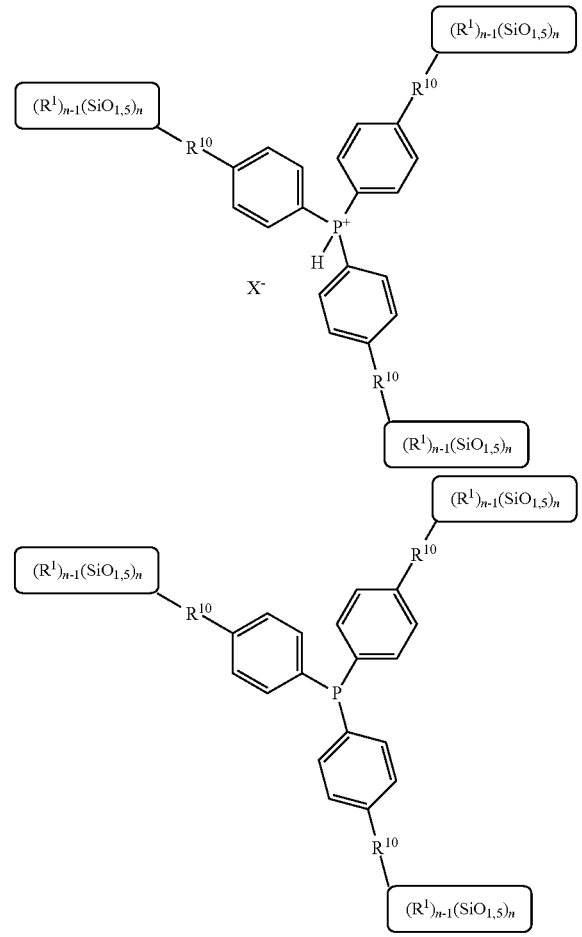

wherein:

$R^{10}$ is the same or different branched or linear $C_1$-$C_{20}$ alkyl chains, cyclo alkyl, $C_1$-$C_{20}$ alkoxy, aryl, aryloxy, arylalkyl groups, substitution pattern also includes further POSS fragments having the same or different structure. $R^{10}$ may also be multiply substituted halogen alkyl, unsubstituted or substituted aryl groups and substituted alkyl groups, aryloxy, hetaryloxy groups.

Additionally the alkyl chain can contain further complexing moieties like imidazol derivatives (formula XII):

XII

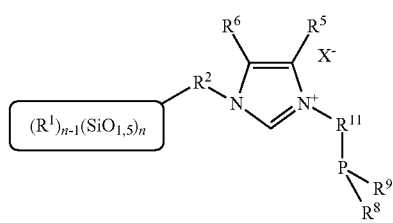

-continued

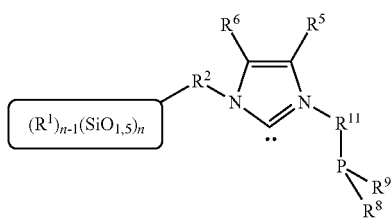

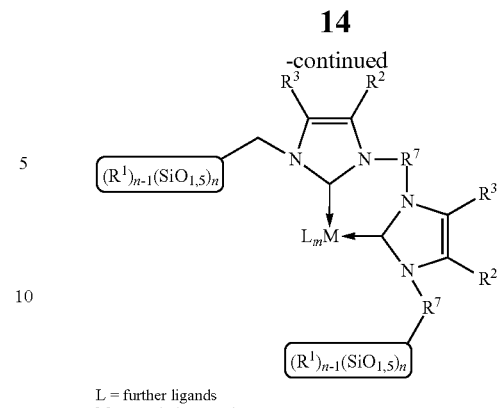

L = further ligands
M = transiotion metal

Due to their size the POSS linked ligands according to the present invention can be considered as being nanoparticle anchored ligands. They can be used in metal catalyzed reactions in combination with nanofiltration technology. The nanometer-sized POSS-molecule to which the catalyst is linked allows specific filtration of the reaction products and other components where the nano-anchored catalyst remains within the membrane sphere. Most importantly high molecular weights of these ligands lead to the corresponding transition metal catalysts with molecular weights ranging from 1500 to 3000, which allows synthesis and filtration of larger sized molecules.

This methodology allows not only simplified separation of the metal catalyst from the organic components. Furthermore repeated multicycled processes and of course continuous processes are feasible as well.

Preferred examples of transition metal complexes with different POSS linked ligands are given below:

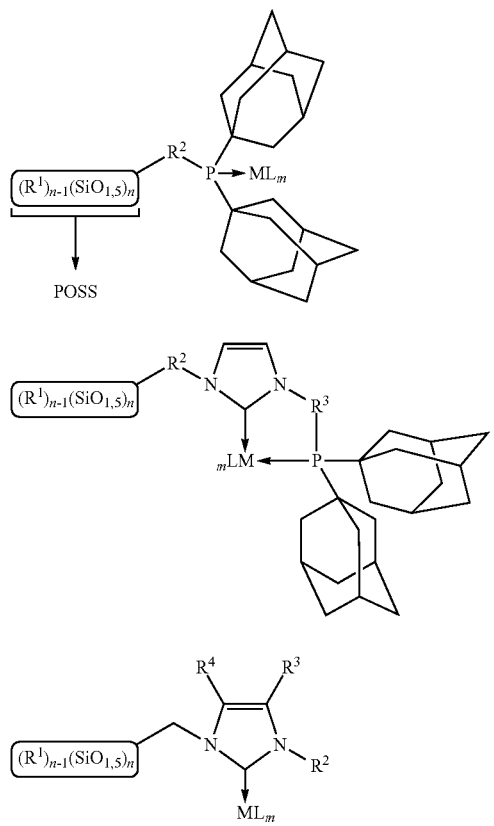

The corresponding transition metal complexes, preferably palladium complexes can be obtained and used in cross-coupling reactions in two ways: 1. they can be isolated after reaction of the phosphonium or imidazolium salts with bases and subsequent addition of a particular palladium source or 2. the active catalyst species can be obtained in the reaction mixture containing both catalyst compounds and the cross-coupling reaction partners in situ during the cross-coupling reaction in which a base is used in order to e.g. activate the palladium precatalyst or generate the active boronate species e.g. in the Suzuki-Miyaura reaction which is essential for the reaction.

Exemplary Synthesis of POSS-Linked Phosphine Ligands and or their Salts

Since most alkyl substituted free phosphines are prone to oxidation when exposed to air, it is far better to store these compounds as their phosphonium salts. The phosphonium salts are very stable compounds to moisture and air that can be stored for a very long time. The syntheses of the ligand salts are straightforward by simple reactions of polysilsesquioxane halides and the corresponding imidazole- and phosphine substrates.

The POSS linked phosphonium salts can be obtained by simple conversion of different POSS-halides having different chain lengths (scheme 1) with a phosphine. In this particular example the preferred bisadamantyl substituted phosphine is used since this phosphine substitution pattern is found in benchmark cataCXiumA®, which has proven to be a superior ligand in particularly manifold palladium-catalyzed cross-coupling reactions. Connecting the POSS cube with bisadamantylphosphine via an unbranched alkyl chain leads to a ligand structure which is very close to that found in cataCXiumA®.

scheme 1

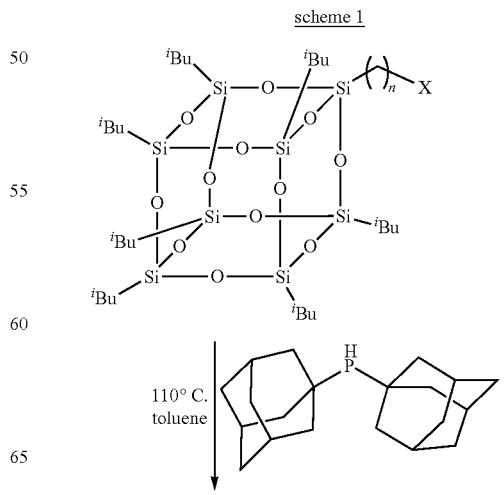

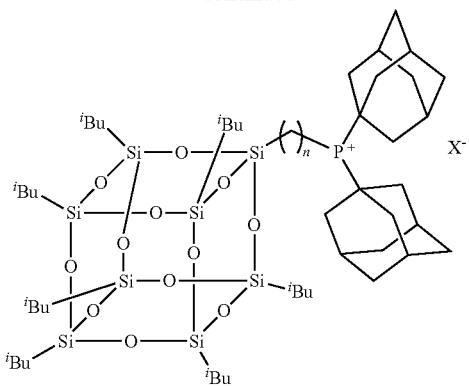

X = Br, I
n = 3, 5, 10

This straight forward synthesis enables simple variation in both chain length between the phosphorus atom and the POSS cube and the moieties on the P-atom.

Exemplary Synthesis of Imidazole-Based NHC-Ligands or their Salts

From the group of imidazole-based NHC-type ligands the salts can be obtained simple reactions starting from POSS-halides and corresponding imidazole (scheme 2, left). For the synthesis of singly imidazole substituted POSS-derivatives, the POSS halides were added slowly two a melt of 10-30 fold excess of imidazol. Simple take-up of the crude product in water and extraction with ether gave the products in excellent yields and high purity.

The syntheses of symmetrically bis-POSS functionalized imidazolium salts were achieved by slight modification of the methodology as demonstrated for the syntheses of mono POSS-substituted imidazoles. The reaction of only two equivalents of imidazole with POSS alkyl halides lead to the clean formation of the corresponding imidazolium salts (scheme 2, right). Addition of at least two equivalents of imidazole is required, because the acid HX which results from the first reaction of one equivalent of imidazole needs to be buffered, otherwise incomplete reaction can occur. Finally, unsymmetrical mesityl-substituted POSS-enlarged imidazolium salts as N-heterocyclic carbene sources can be obtained by the simple protocol as well (scheme 2, top).

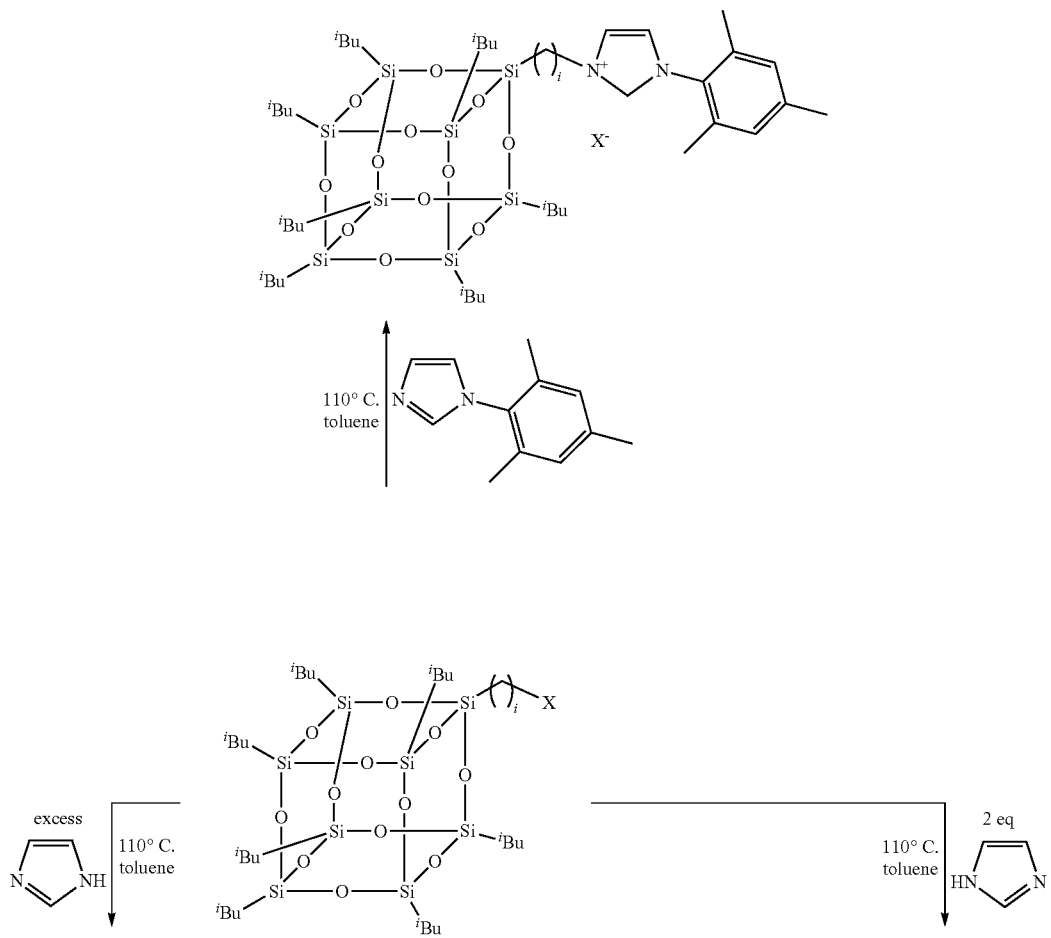

scheme 2

-continued

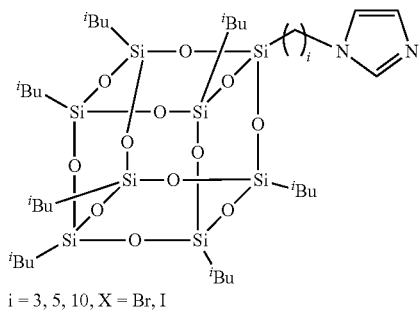

i = 3, 5, 10, X = Br, I

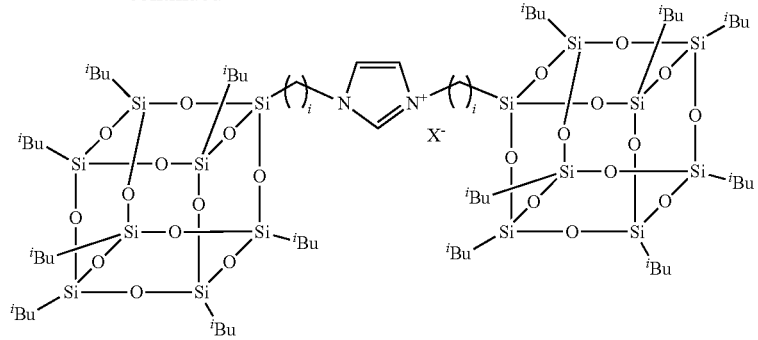

With the mono POSS enlarged imidazoles (from scheme 2) in hands, syntheses of various ligands that bear further POSS-substituted imidazole moieties or even mixed phosphine-NHC ligands were realized. Thus, starting from the mono POSS-substituted imidazole derivatives, in the first step the alkyl bridging moiety was installed (scheme 3, left). To avoid formation of side products, first an excess of the alkylating reagent (1,2-dibromoethane, 1,3-dibromopropane) was heated to 120° C. and the corresponding POSS-substituted imidazole derivative was added portionwise giving rise to the imidazolium salts.

On the other hand addition of 0.5 eq. of the alkylating reagent to the molten POSS-substituted imidazole derivative lead to the formation of the alkyl bridged dimer in very good yields (scheme 3, right).

scheme 3

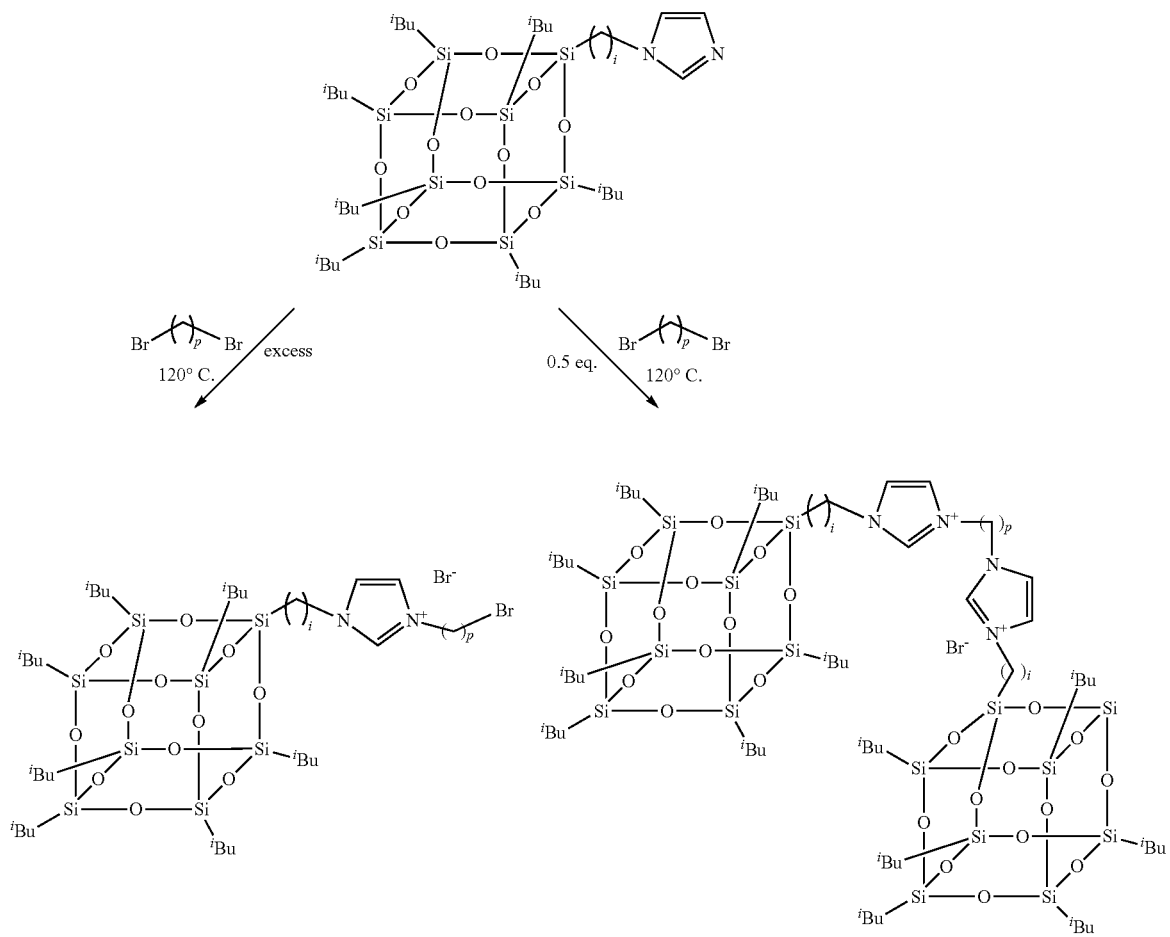

i = 3, 5, 10
p = 1, 2, 3

The mixed phosphine-imidazolium-based NHC type of ligands are obtained by conversion of the POSS-containing singly alkylated imidazolium salts by treating with phosphines or their mineral salts respectively:

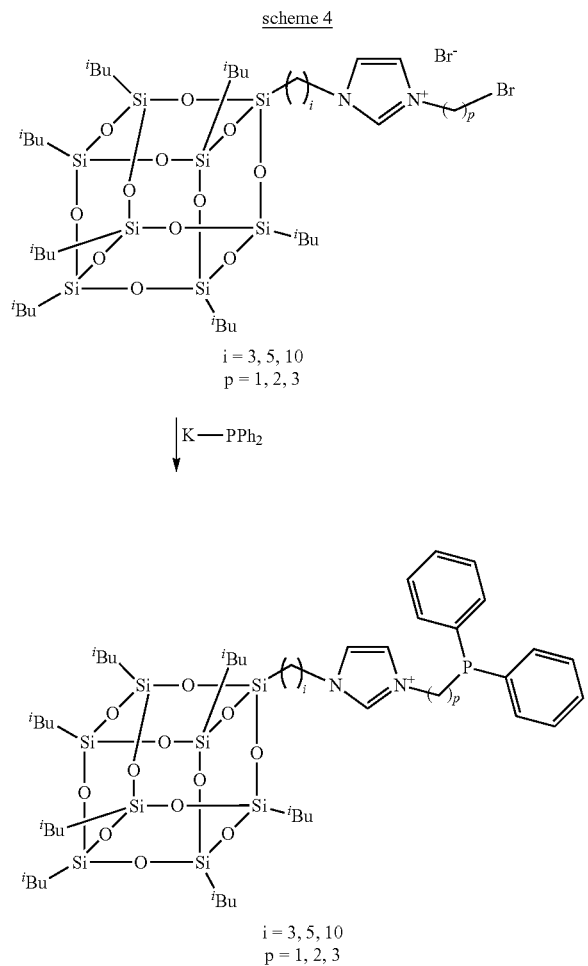

scheme 4 i = 3, 5, 10
p = 1, 2, 3

The symmetric POSS-substituted bis-imidazolium salts can be converted into the corresponding bis-NHC-transition metal complexes by treatment with a base and subsequent addition of an appropriate metal source. As an interesting candidate for general industrial application, Palladium was taken as metal of choice for the synthesis of various carbene- and phosphine complexes and their employment in C—C- and C—N-coupling reactions.

Furthermore new efficient and straightforward synthesis methods were established for the manufacture of these ligands to design new transition metal catalysts.

Application of the Ligands and Catalysts in C—C- and C—N Cross-Coupling Reactions The POSS-based phosphine ligands were tested in a C—C cross-coupling reaction (Heck-Mizoroki reaction, scheme 5).

scheme 5

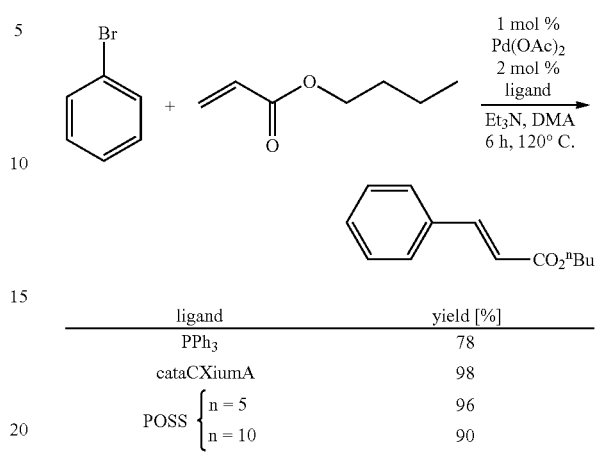

| ligand | | yield [%] |
|---|---|---|
| PPh₃ | | 78 |
| cataCXiumA | | 98 |
| POSS | n = 5 | 96 |
| | n = 10 | 90 |

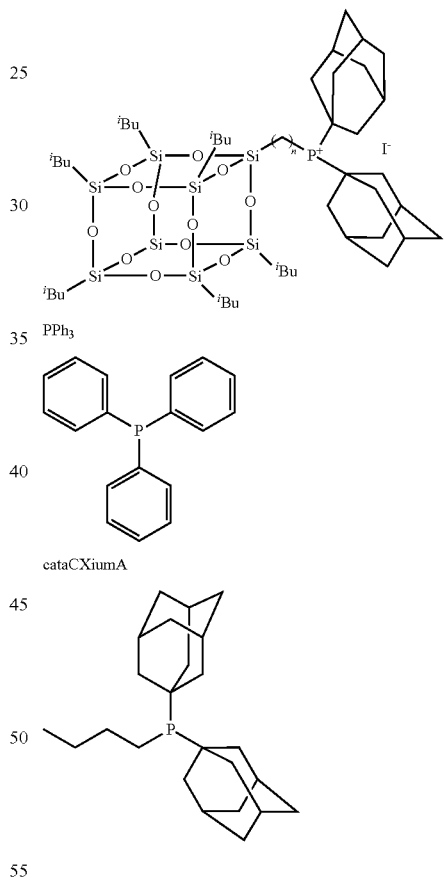

cataCXiumA

These results demonstrate that the POSS-enlarged analogues of the benchmark ligand cataCXiumA® display also an outstanding performance in cross-coupling reactions.

Some of the described imidazole derived N-heterocyclic carbene ligands which have been POSS enlarged were converted to various palladium catalysts. From these the iodine p-bridged dimeric catalyst showed the highest activity in a C—N cross-coupling reaction (Buchwald-Hartwig reaction) in combination with POSS-enlarged cataCXiumA® ligands and were compared with further benchmark phosphine ligands (scheme 6).

scheme 6

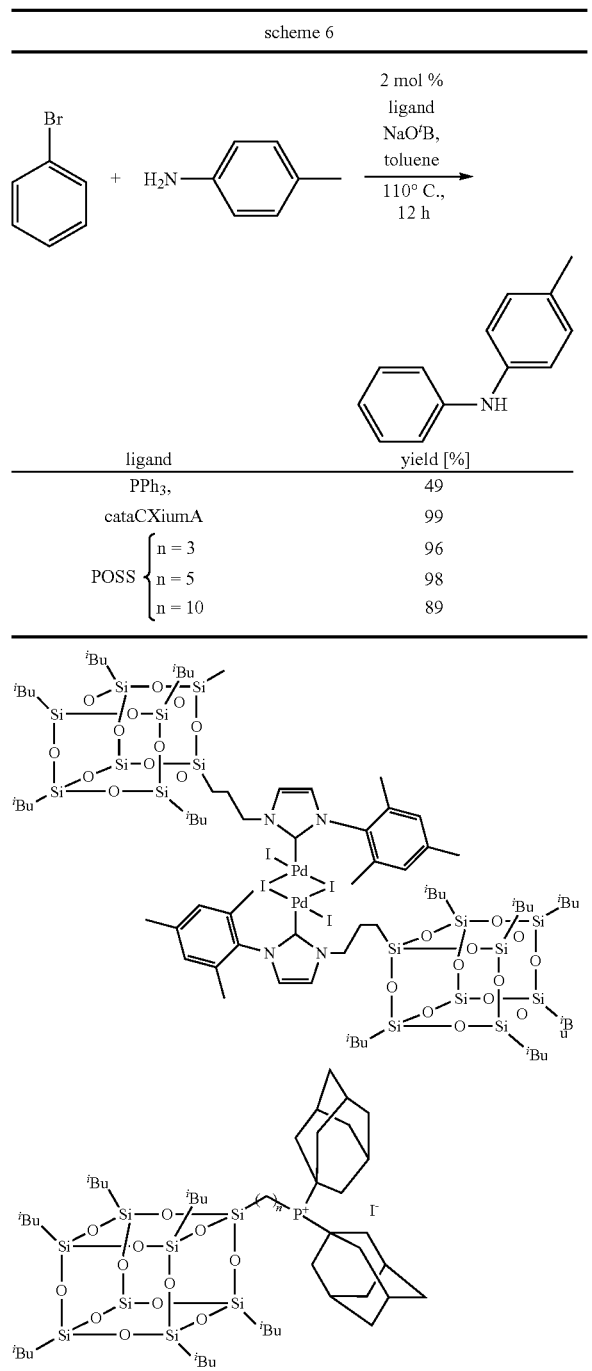

| ligand | yield [%] |
|---|---|
| PPh₃ | 49 |
| cataCXiumA | 99 |
| POSS n = 3 | 96 |
| POSS n = 5 | 98 |
| POSS n = 10 | 89 |

Importantly, the highest catalytic activities were observed when the enlarged catalyst systems were used together with the POSS-enlarged cataCXiumA® ligands.

In conclusion, the enlarged structure properties of POSS-based phosphine ligands and imidazole-based NHC-palladium catalysts fulfil all of the requirements which were set for the application in cross-coupling reactions in connection with membrane-filtration technology.

EXAMPLES

Synthesis Off POSS-Enlarged Ligands

General. The $^{31}$P- and $^{1}$H-NMR-spectra were measured on Bruker DRX 500 (500 MHz) spectrometer. For the $^{1}$H-NMR-spectra the chemical shifts were given in ppm from tetramethylsilane as an internal standard (0.00 ppm) or the solvent residue peaks (CDCl₃: 7.26 ppm, CD₂Cl₂: 5.26 ppm). The chemical shifts of the $^{31}$P resonances were determined relative to phosphoric acid (H₃PO₄) as an internal standard (0.00 ppm). Peak multiciplities were abbreviated as: s, singlet; d, dublet, t, triplet, qr, quartet, qn, quintet, sep, septet; m, multiplet. All solvents and chemicals were used as purchased. Reagents and solvents were purchased from Aldrich. All POSS starting materials were purchased from Hybrid Catalysis. Di-(1-adamantyl)phosphine is an in-house product of EVONIK-DEGUSSA GmbH.

General Procedure for the Syntheses of POSS-Phosphonium Salts:

Slight excess of the POSS starting material (1.1 equivalents related to the phosphine) was dissolved in toluene (or xylene) in a round bottomed flask fitted with a stirring bar by heating in an oil bath at 110° C. (130° C. for xylene, which is also the reaction temperature). The reaction mixture was stirred 2-4 hours whereupon the product precipitates as a solid.

Next the solid was isolated by filtration and was washed with hexane. The products are snow-white solids whereas the iodide salts become yellowish after longer storing.

Example 1

Isobutyl-POSS-propyl-3-di-(1-adamantyl)-phosphonium iodide 8.61 g (8.7 mmol) of Propyliodoisobutyl POSS was dissolved in 80 ml of xylene according to the general procedure. Then 2.40 g (7.9 mmol) Di(1-adamantyl)phosphine was added. After 12 h reaction time the reaction was accomplished. Crude product was purified as described. 7.5 g (73%) of a snow-white product was yielded. $^{31}$P-NMR (162 MHz, CDCl₃): δ=19.08 ppm.

Example 2

Isobutyl-POSS-pentyl-5-di-(1-adamantyl)-phosphonium iodide 5.12 g (5 mmol) of Pentyliodoisobutyl POSS was dissolved in 60 ml of toluene according to the general procedure. Then 1.46 g (4.8 mmol) Di(1-adamantyl)phosphine was added. After 12 h reaction time the reaction was accomplished. Purification of the crude product afforded 5.86 g (92%) of a snow-white product. $^{31}$P-NMR (162 MHz, CDCl₃): δ=22.93 ppm.

Example 3

Isobutyl-POSS-decyl-10-di-(1-adamantyl)-phosphonium iodide 1.02 g (0.94 mmol) of Decyliodoisobutyl POSS was dissolved in xylene at 130° C. and 278 mg (0.92 mmol) Di(1-adamantyl)phosphine was added. After 12 h reaction time the reaction was accomplished. Purification of the crude product afforded 600 mg (49%) of a snow-white to slightly yellow product. $^{31}$P-NMR (162 MHz, CDCl₃): δ=21.21 ppm.

General Procedure for the Syntheses of POSS-Imidazolium Salts:

The procedure is similar to the previous. Only variations are: Toluene as solvent was used and the reaction temperature is 110° C. The reaction mixture stirred 12-16 hours whereupon the product precipitates as a solid. Next toluene was added as much as it is required to keep the reaction mixture liquid and mobile. The purification of the crude product is accomplished on a silica gel column (solvent:mixtures hexane-ethyl acetate 10:1, then methanol.

Example 4

Isobutyl-POSS-propyl-3-(1-mesityl)-imidazolium iodide 5.00 g (5.1 mmol) of Propyliodoisobutyl POSS was dissolved in 60 ml of toluene according to the general procedure at 110° C. Then 860 mg (4.6 mmol) of 1-Mesitylimidazole was added. After 4 h the reaction was accomplished. Work-up and purification according to the general procedure resulted in the isolation of 4.58 g (78%) pure product as a white solid.

$^1$H-NMR (500 MHz, CDCl$_3$): δ 0.61, (m, 16H, Si—CH$_2$— and 7×POSS-Si—CH$_2$—), 0.96 (m, 7×(CH$_3$)$_2$CH), 1.85 (m, 7H, 7×Si—CH$_2$—CH—), 2.07 (m, 2H, Si—CH$_2$—CH$_2$—CH$_2$—), 2.11 (s, 6H, 2 o-CH$_3$-Ph), 2.35 (s, 3H, p-CH$_3$-Ph), 4.76 (bt, 2H, —CH$_2$—N$^{Im}$), 7.03 (s, 2H, 2 m-Ph-H), 7.18 (s, 1H, 5-H$^{Im}$), 7.51 (s, 1H, 4-H$^{Im}$), 10.18 (s, 1H, 2-H$^{Im}$).

Example 5

Isobutyl-POSS-pentyl-5-(1-mesityl)-imidazolium iodide 2.00 g (2.1 mmol) of Propylbromoisobutyl POSS was dissolved in 60 ml of toluene according to the general procedure at 110° C. Then 367 mg (1.9 mmol) of 1-Mesitylimidazole was added. After 16 h the reaction was accomplished. Work-up and purification according to the general procedure resulted in the isolation of 3.05 g (67%) pure product as a white solid.

$^1$H-NMR (500 MHz, CDCl$_3$): δ 0.58-0.61, (m, 16H, Si—CH$_2$— and 7×POSS-Si—CH$_2$—), 0.96, (m, 42H 7×(CH$_3$)$_2$CH), 1.43 (m, 4H, 2-CH2-), 1.85 (m, 7H, 7×CH), 1.95 (m, 2H, —CH2-), 2.08 (s, 6H, 2 o-CH$_3$-Ph), 2.35 (s, 3H, 2 m-Ph-H), 4.66 (t, J=7.0 Hz, 2H, —CH$_2$—N), 7.01 (s, 2H, 2 m-Ph-H), 6.48 (s, 1H, 5-H$^{Im}$), 7.26 (m, 1H, 5-H$^{Im}$), 7.70 (m, 1H, 4-H$^{Im}$) 10.06 (s, 1H, 2-Him).

Example 6

Isobutyl-POSS-decyl-10-(1-mesityl)-imidazolium iodide 5.00 g (4.8 mmol) of Decylbromoisobutyl POSS was dissolved in 60 ml of toluene according to the general procedure at 110° C. Then 816 mg (4.4 mmol) of 1-Mesitylimidazole was added. After 1 h the reaction was accomplished. Work-up and purification according to the general procedure resulted in the isolation of 4.94 g (92%) pure product as a white solid.

$^1$H-NMR (500 MHz, CDCl$_3$): δ 0.57-0.61, (m, 16H, Si—CH$_2$— and 7×POSS-Si—CH$_2$—), 0.96, (m, 42H 7×(CH$_3$)$_2$CH), 1.25 (m, 8H, 4-CH2-), 1.37 (m, 6H, 3-CH2-), 1.86 (sep, J=6.7 Hz, 7H, 7×POSS-CH), 1.99 (m, 2H, —CH2-), 2.08 (s, 6H, 2 o-CH$_3$-Ph), 2.35 (s, 3H, 2 m-Ph-H), 4.66 (t, J=7.0 Hz, 2H, —CH$_2$—N), 7.00 (s, 2H, 2 m-Ph-H), 6.48 (s, 1H, 5-H$^{Im}$), 7.19 (m, 1H, 5-H$^{Im}$), 7.72 (m, 1H, 4-H$^{Im}$) 10.50 (s, 1H, 2-H$^{Im}$).

General Procedure for the Syntheses of POSS-Imidazole Derivatives 10-40 fold excess of imidazole was dissolved in toluene in a round bottomed flask at 110° C. To this solution the POSS compounds were added. The reaction mixture was stirred from 4 h to 24 h at this temperature. Then excess imidazole was removed by extraction with water and the product was extracted with diethyl ether. After a short silica-gel column filtration (ethyl acetate) the product was separated from the bis-POSS imidazole side product.

Example 7

Isobutyl-POSS-propyl-3-imidazole 14.6 g (214 mmol) of imidazole was dissolved in 250 ml of toluene and 5.77 g (5.85 mmol) of Isobutyl-POSS-propyl-3-iodide was added portionwise to the solution. Work-up gave 5.27 g (97%) of pure snow-white product.

$^1$H-NMR (500 MHz, CDCl$_3$): δ 0.60 (m, 16H, Si—CH$_2$— and 7×POSS-Si—CH$_2$—), 0.95, (m, 42H 7×(CH$_3$)$_2$CH), 1.85 (m, 9H, 7×POSS-CH, CH$_2$), 3.91 (t, J=7.1 Hz, 2H, CH$_2$), 6.87, 7.06, 7.44 (3 m, 1H each, Imidazole-H).

Example 8

Isobutyl-POSS-pentyl-5-imidazole 5.37 g (79 mmol) of imidazole were dissolved in 60 ml of toluene at the given temperature. To this solution 2.0 g (3.95 mmol) of Isobutyl-POSS-pentyl-5-iodide was added. Workup gave 3.26 g (87% yield) of the product as a white solid.

$^1$H-NMR (500 MHz, CDCl$_3$): δ 0.60 (m, 16H, Si—CH$_2$— and 7×POSS-Si—CH$_2$—), 0.95, (m, 42H 7×(CH$_3$)$_2$CH), 1.34 (m, 2H, CH$_2$), 1.44 (m, 2H, CH$_2$), 1.77 (m, 2H, CH$_2$), 1.85 (sep, J=6.7 Hz, 7×POSS-CH), 3.91 (t, J=7.3 Hz, 2H, CH$_2$), 6.89, 7.05, 7.46 (3 m, 1H each, Imidazole-H).

Example 9

Isobutyl-POSS-decyl-10-imidazole 10.6 g (157 mmol) of imidazole was dissolved in 200 ml of toluene at the given temperature and was treated with 8.5 g (7.85 mmol) of Isobutyl-POSS-decyl-10-iodide. The workup followed after 12 h reaction time and gave 5.56 g (61% yield) of a white solid.

$^1$H-NMR (500 MHz, CDCl$_3$): δ 0.60 (m, 16H, Si—CH$_2$— and 7×POSS-Si—CH$_2$—), 0.96, (m, 42H 7×(CH$_3$)$_2$CH), 1.25-1.30 (m, 12H, CH$_2$), 1.38 (m, 2H, CH$_2$), 1.77 (m, 2H, CH$_2$), 1.85 (sep, J=6.7 Hz, 7×POSS-CH), 3.91 (t, J=7.2 Hz, 2H, CH$_2$), 6.89, 7.05, 7.46 (3 m, 1H each, Imidazole-H).

Example 10

1,3-Bis(isobutyl-POSS-pentyl)-imidazolium iodide 6.0 g (5.92 mmol) of Isobutyl-POSS-pentyl-5-iodide was dissolved in 70 ml of toluene at 110° C. with stirring. Then two equivalents (806 mg, 18.4 mmol) of imidazole which was dissolved in 3 ml hot toluene was added. After 12 h of stirring the reaction was complete. The crude product was treated with water-diethylether. The aqueous phase was discarded and the organic phase was dried using magnesium sulphate. After removal of the solvent 5.17 g (82% yield) of a yellow solid was isolated.

$^1$H-NMR (500 MHz, CDCl$_3$): $^1$H-NMR (500 MHz, CDCl$_3$): δ 0.60 (m, 32H, 2×Si—CH$_2$— and 14×POSS-Si—CH$_2$—), 0.95, (m, 84H, 14×(CH$_3$)$_2$CH), 1.31-1.45 (m, 8H, 4×CH$_2$), 1.75-1.93 (m, 18H, 2CH$_2$ and 14×POSS-CH), 3.91

(t, J=7.2 Hz, 2H, CH$_2$), 4.33 (t, J=7.5 Hz, 2H, 2CH$_2$), 6.89, 7.05, 10.57 (3 m, 1H each, Imidazole-H).

Example 11

1-(Isobutyl-POSS-propyl)-3-(bromoetyl)imidazolium bromide 8.59 g (46 mmol) of dibromoethane was heated to 120° C. and 2.18 g (2.3 mmol) of Isobutyl-POSS-pentyl-3-imidazole was added portionwise with stirring. After 2 h reaction time the crude reaction mixture was purified according to the general procedure and 1.09 (42% yield) of a white solid as product was isolated.

$^1$H-NMR (500 MHz, CDCl$_3$): δ 0.59 (m, 16H, Si—CH$_2$— and 7×POSS-Si—CH$_2$—), 0.95, (m, 42H 7×(CH$_3$)$_2$CH), 1.35, 1.44 (2 m, 2H each, 2CH$_2$), 1.85 (m, 9H, —CH$_2$—, 7×(CH$_3$)$_2$CH), 3.90 (t, J=5.9 Hz, 2H, —CH$_2$—), 4.21 (m, 2H, —CH$_2$—), 4.71 (t, J=5.8 Hz, 2H, —CH$_2$—), 7.66, 7.87, 9.58 (3 m, 1H each, imdazole-H).

Example 12

1-(Isobutyl-POSS-propyl)-3-(3-brompropyl)imidazolium bromide 13.4 g (66 mmol) of 1,3-dibromopropane was heated to 120° C. Then 3.1 g (3.3 mmol) of Isobutyl-POSS-propyl-3-imidazole portionwise over 1 h. After 6 h reaction time the crude reaction mixture was purified by column chromatography using silica gel (solvents: hexane-ethyl acetate 10:1, then methanol). The product was obtained as a white solid (2.75 g, 74% yield).

$^1$H-NMR (500 MHz, CDCl$_3$): δ 0.61 (m, 16H, —Si—CH$_2$, 7×POSS-Si—CH$_2$—), 0.95, (m, 42H 7×(CH$_3$)$_2$CH), 1.85 (sep, J=6.7 Hz, 7×POSS-CH 2.04 (m, 2H, CH$_2$, 7×POSS-CH), 2.63 (m, 2H, CH$_2$), 3.54 (t, J=6.0 Hz, 2H, CH$_2$), 4.36 (t, J=7.1 Hz, 2H, CH$_2$), 7.17, 7.46, 10.88 (3 m, 1H each, Imidazole-H).

Example 13

1-(Isobutyl-POSS-pentyl)-3-(3-brompropyl)imidazolium bromide 6.0 g 30 mmol) of 1,3-dibromopropane was heated to 120° C. Then 1.56 g (1.63 mmol) of Isobutyl-POSS-pentyl-3-imidazole was added. After 6 h reaction time the crude reaction mixture was purified by column chromatography using silica gel (solvents: hexane-ethyl acetate 10:1, then methanol). The product was obtained as a white solid (1.70 g, 90% yield).

$^1$H-NMR (500 MHz, CDCl$_3$): δ 0.60 (m, 16H, —Si—CH$_2$, 7×POSS-Si—CH$_2$—), 0.95, (m, 42H 7×(CH$_3$)$_2$CH), 1.40-1.46 (m, 4H, 2CH$_2$), 1.82-1.92 (m, 9H, CH$_2$, 7×POSS-CH), 2.62 (m, 2H, CH$_2$), 3.48 (m, 2H, CH$_2$), 4.30 (m, 2H, CH$_2$), 4.65 (m, 2H, CH$_2$), 7.21, 7.41, 10.81 (3 m, 1H each, Imidazole-H).

Example 14

1,2-bis[(3-isobutyl-POSS-pentyl]imidzaloyl-ethane 1.63 g (1.71 mmol, 1.5 eq.) of Isobutyl-POSS-pentyl-5-imidazole was molten at 130° C. with the assistance of 3 ml toluene. To this melt 227 mg (1.21 mmol) of 1,2-dibromoethane which was dissolved in 0.5 ml of toluene was added via a pipette. The solvent together with excess of 1,2-dibromoethane were removed in vacuo and 1.51 g (77% yield) of the pure product was obtained as a white solid.

$^1$H-NMR (500 MHz, CDCl$_3$): δ 0.61 (m, 16H, —Si—CH$_2$, 7×POSS-Si—CH$_2$—), 0.96, (m, 42H 7×(CH$_3$)$_2$CH), 1.32-1.47 (m, 4H, 2CH$_2$), 1.78-1.91 (m, 9H, CH$_2$, 7×POSS-CH), 3.96 (m, 2H, CH$_2$), 4.14 (m, 2H, bridge-CH$_2$), 6.93, 7.69, 10.81 (3 m, 1H each, Imidazole-H).

Example 15

1,3-bis[(3-isobutyl-POSS-pentyl]imidzaloyl-propane 2.0 g (2.13 mmol) of Isobutyl-POSS-pentyl-5-imidazole was molten at 130° C. with the assistance of 3 ml of toluene. To this melt a toluene solution of 215 mg (1.065 mmol) 1,3-dibromopropane was added via pipette. The mixture was stirred 2 h at this temperature. The reaction is completed when the melt becomes ductile. The solvent is removed in vacuo and 2.0 g (81% yield) of the pure product is isolated as a white solid.

$^1$H-NMR (500 MHz, CDCl$_3$): δ 0.61 (m, 16H, —Si—CH$_2$, 7×POSS-Si—CH$_2$—), 0.96, (m, 42H 7×(CH$_3$)$_2$CH), 1.38-1.45 (m, 8H, 4 CH$_2$), 1.82-1.89 (m, 18H, 2×CH$_2$, 14×POSS-CH), 2.93 (m, 2H, bridge-CH$_2$), 4.13 (m, 4H, CH$_2$), 4.21 (m, 4H, 2×CH$_2$), 4.77 (m, 4H, 2 bridge-CH$_2$), 7.14, 8.23, 10.25 (3 m, 1H each, Imidazole-H).

The invention claimed is:

1. A catalyst comprising a transition metal and a polyhedral oligomeric silsesquioxane (POSS)-linked ligand of formula (I):

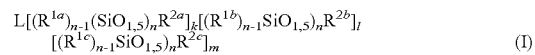

wherein: $(R^{1a,b,c})_{n-1}(SiO_{1.5})_n$ is a polyhedral oligomeric silsesquioxane (POSS) with n=4, 6, 8, 10, 12, 14, 16 or 18 and $R^{1a}$, $R^{1b}$, $R^{1c}$ are each independently selected from the group consisting of the same or different branched or linear $C_1$-$C_{20}$ alkyl chains, cyclo alkyl, $C_1$-$C_{20}$ alkoxy, aryl, aryloxy, heteroaryl and arylalkyl groups, k, l, and m are 0 or 1, provided that k+l+m≥1, $R^{2a}$, $R^{2b}$, $R^{2c}$ are spacers that bind the polyhedral oligomeric silsesquioxane (POSS) to the ligand L, and are each independently selected from the group consisting of linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, $C_1$-$C_{20}$ alkyl halogenide, annulated aryl or heteroaryl, and $C_3$-$C_{10}$ cyclic alkyl groups which, in turn, may each be further substituted with one or more groups selected from: hetero atoms or aryl groups, ether, polyether, polythioether, amino, and aryl bridged alkyl chain where the aryl moiety can be further substituted and ligand L is an N-heterocyclic carbene;

wherein said catalyst has a molecular weight of 1500 to 3000 g/mol;

and wherein:

said POSS-linked ligand is optionally part of a bidentate polyhedral oligomeric silsesquioxane-linked ligand of general formula (III):

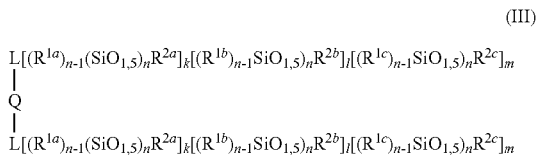

(III)

wherein Q is selected from: a branched or linear substituted or unsubstituted alkyl chain with a chain length ranging from $C_1$ to $C_{20}$ and a unsubstituted or substituted cyclic alkyl, aryl or heteroaryl group where the aryl and heteroaryl moieties can be further substituted;

and wherein said catalyst is:
  i) soluble and catalytically active in one or more organic solvents, thereby permitting homogeneous catalysis in said solvents; and
  ii) filtratable by membrane filtration.

2. The catalyst of claim 1, wherein said POSS-linked ligand is part of a bidentate polyhedral oligomeric silsesquioxane-linked ligand of general formula (III):

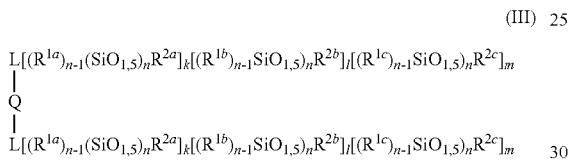

(III)

wherein Q is selected from: a branched or linear substituted or unsubstituted alkyl chain with a chain length ranging from $C_1$ to $C_{20}$ and a unsubstituted or substituted cyclic alkyl, aryl or heteroaryl group where the aryl and heteroaryl moieties can be further substituted.

3. The catalyst of claim 1, wherein $R^{1a}, R^{1b}, R^{1c}$ are unsubstituted branched $C_1$-$C_{20}$ alkyl chains and wherein the ligand in said POSS-linked ligand exhibits improved solubility in toluene compared to the ligand when not in said POSS-linked ligand.

4. The catalyst of claim 1, wherein $R^{2a}, R^{2b}, R^{2c}$ are each a linear $C_1$-$C_{20}$ alkyl and wherein the ligand in said POSS-linked ligand exhibits improved solubility in toluene compared to the ligand when not in said POSS-linked ligand.

5. The catalyst of claim 1, wherein k=1, l=0, and m=0.

6. The catalyst of claim 1, wherein said POSS-linked ligand is

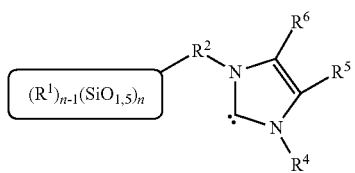

wherein:
$R^1$ is selected from the group consisting of the same or different branched or linear $C_1$-$C_{20}$ alkyl chains, cyclo alkyl, $C_1$-$C_{20}$ alkoxy, aryl, aryloxy, heteroaryl and arylalkyl groups,
$R^2$ is selected from the group consisting of linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, $C_1$-$C_{20}$ alkyl halogenide, annulated aryl or heteroaryl, $C_3$-$C_{10}$ cyclic alkyl groups which, in turn, may each be further substituted with one or more groups selected from: hetero atoms or aryl groups, ether, polyether, polythioether, amino, aryl bridged alkyl chain, where the aryl moiety can be further substituted;

$R^4$, $R^5$ and $R^6$ are each independently selected from the group consisting of hydrogen, linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, substituted halogen aryl or heteroaryl, $C_1$-$C_{20}$ alkyl halogenide, annulated aryl or heteroaryl, and $C_3$-$C_{10}$ cyclic alkyl groups which in turn may each be further substituted with one or more groups selected from hetero atom or aryl groups.

7. The catalyst of claim 1, wherein said transition metal is palladium.

8. The catalyst of claim 7, wherein said POSS-linked ligand is part of a bidentate polyhedral oligomeric silsesquioxane-linked ligand of general formula (III):

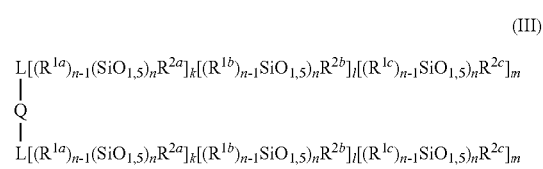

(III)

wherein Q is selected from: a branched or linear substituted or unsubstituted alkyl chain with a chain length ranging from $C_1$ to $C_{20}$ and a unsubstituted or substituted cyclic alkyl, aryl or heteroaryl group where the aryl and heteroaryl moieties can be further substituted.

9. The catalyst of claim 7, wherein $R^{1a}, R^{1b}$, and $R^{1c}$ in said POSS-linked ligand are unsubstituted branched $C_1$-$C_{20}$ alkyl chains.

10. The catalyst of claim 7, wherein k=1, l=0, and m=0 in said POSS-linked ligand.

11. A transition metal catalyzed reaction, wherein said reaction is performed in the presence of the catalyst of claim 1.

12. The transition metal catalyzed reaction of claim 11, wherein said reaction is a C—C or a C—N cross coupling reaction.

13. The transition metal catalyzed reaction of claim 12, wherein said reaction utilizes a catalyst comprising palladium as the transition metal.

14. The catalyst of claim 1, wherein said POSS-linked ligand is selected from the group consisting of:

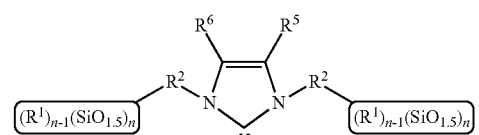

-continued

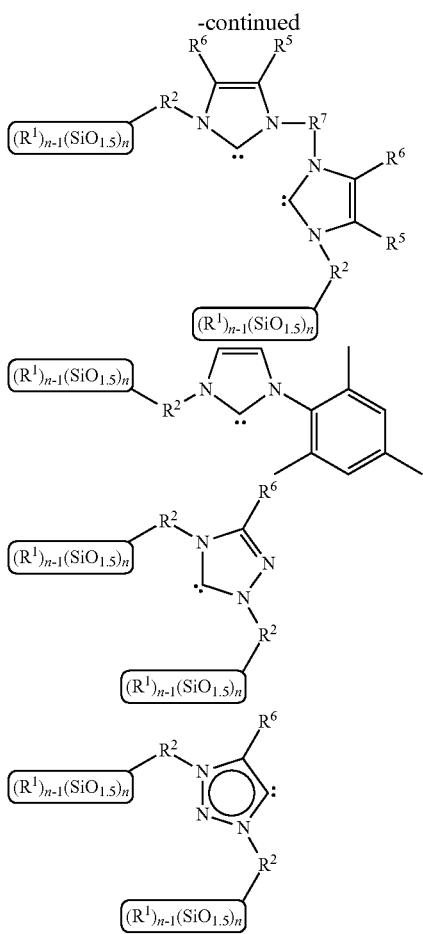

wherein:

each $R^1$ is independently selected from the group consisting of the same or different branched or linear $C_1$-$C_{20}$ alkyl chains, cyclo alkyl, $C_1$-$C_{20}$ alkoxy, aryl, aryloxy, heteroaryl and arylalkyl groups, each $R^2$ is independently selected from the group consisting of linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_i$-$C_{20}$ alkylthio, $C_1$-$C_{20}$ carboxylate, aryl or heteroaryl, $C_{10}$-$C_{20}$ alkyl halogenide, annulated aryl or heteroaryl, $C_3$-$C_{10}$ cyclic alkyl groups which, in turn, may each be further substituted with one or more groups selected from: hetero atoms or aryl groups, ether, polyether, polythioether, amino, aryl bridged alkyl chain where the aryl moiety can be further substituted, $X^-$ is a mono- or polyvalent organic or inorganic anion, $R^3$, $R^5$, $R^6$ are each independently selected from the group consisting of: hydrogen, linear or branched $C_1$-$C_{20}$ alkyl, $C_3$-$C_{10}$ cyclic alkyl, $C_1$-$C_{20}$ alkoxy, $C_2$-$C_{20}$ alkenyl, $C_2$-$C_{20}$ alkenyloxy, aryloxy, $C_1$-$C_{20}$ alkylthio, $C_1$-$C_{20}$ carboxylate, aryl or heteroaryl, substituted halogen aryl or heteroaryl, $C_1$-$C_{20}$ alkyl halogenide, annulated aryl or heteroaryl, and $C_3$-$C_{io}$ cyclic alkyl groups, which in turn may each be further substituted with one or more groups selected from hetero atom or aryl groups and $R^7$ is substituted or unsubstituted linear or branched $C_1$-$C_{10}$ alkyl chain.

15. The catalyst of claim 1, wherein said transition metal is Ru(III).

16. The transition metal catalyzed reaction of claim 12, wherein said transition metal is Ru(III).

* * * * *